United States Patent
Martin et al.

(10) Patent No.: US 10,674,910 B1
(45) Date of Patent: *Jun. 9, 2020

(54) ICU TELEMEDICINE SYSTEM FOR VARIED EMR SYSTEMS

(71) Applicant: Epic Systems Corporation, Verona, WI (US)

(72) Inventors: Stirling Martin, Madison, WI (US); Aaron Webb, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 264 days.

This patent is subject to a terminal disclaimer.

(21) Appl. No.: 15/693,798

(22) Filed: Sep. 1, 2017

Related U.S. Application Data

(63) Continuation of application No. 13/597,959, filed on Aug. 29, 2012, now Pat. No. 9,750,408.

(60) Provisional application No. 61/528,362, filed on Aug. 29, 2011.

(51) Int. Cl.
| | | |
|---|---|---|
| *G16H 20/00* | (2018.01) | |
| *A61B 5/00* | (2006.01) | |
| *G16H 40/67* | (2018.01) | |
| *A61B 5/0205* | (2006.01) | |

(52) U.S. Cl.
CPC .......... *A61B 5/0002* (2013.01); *A61B 5/0022* (2013.01); *A61B 5/0205* (2013.01); *G16H 40/67* (2018.01); *A61B 2505/03* (2013.01)

(58) Field of Classification Search
CPC .............................. G16H 40/67; G16H 20/00
See application file for complete search history.

(56) References Cited

U.S. PATENT DOCUMENTS

| | | | |
|---|---|---|---|
| 2003/0028536 A1* | 2/2003 | Singh | H04W 4/029 |
| 2006/0017563 A1* | 1/2006 | Rosenfeld | A61B 5/412 340/539.12 |
| 2013/0218588 A1* | 8/2013 | Kehr | A61B 5/4839 705/2 |

* cited by examiner

*Primary Examiner* — John A Pauls
(74) *Attorney, Agent, or Firm* — Boyle Fredrickson S.C.

(57) ABSTRACT

A computer-implemented patient monitoring system includes a patient data monitoring system on a first computing system, including a patient medical data query engine configured to generate one or more rule execution requests. The monitoring system further includes a network circuit communicating with the medical database system and one or more remote patient care computing devices. The remote care computing devices in turn include a patient medical data repository and a query response engine configured to respond to received rule execution requests. Responding to rule execution requests includes verifying the validity of a rule execution request, identifying data in the patient medical data repository responsive to the rule execution request, and transmitting response patient medical data responsive to the rule execution request.

18 Claims, 7 Drawing Sheets

ICU TELEMEDICINE SYSTEM FOR VARIED EMR SYSTEMS

CROSS-REFERENCE TO RELATED APPLICATION

This application is a continuation and claims the benefit of U.S. Non-provisional application Ser. No. 13/597,959 filed Aug. 29, 2012 and Provisional Application No. 61/528,362 filed Aug. 29, 2011, the entire contents of which are hereby expressed incorporated by reference into the present application.

BACKGROUND OF THE INVENTION

The present invention relates to telemedicine systems and in particular telemedicine systems useful for intensive care units.

Intensive care units (ICUs) are, for example, departments in a hospital dedicated to treating patients who need constant care or who are subject to life-threatening conditions. Such ICUs may include those specializing in neonatal, pediatric, psychiatric, coronary care, and/or post anesthesia care among other specialties. ICUs typically provide specialized equipment such as ventilators, dialysis equipment, defibrillators, and monitoring equipment which automatically monitor pulse, blood pressure, breathing, body temperature and the like.

ICUs often have high staffing needs, for example, requiring critical care nurses who can respond to deterioration in patient condition and physicians specializing in ICU practice who are available for immediate consultation with respect to developing problems. This high level of staffing can impose a significant burden to smaller facilities particularly overnight when other facility staffing is normally reduced.

To address this problem, ICU telemedicine has been developed allowing healthcare professionals specializing in ICU care but located at a remote command center to monitor multiple scattered ICU units via computer and communication networks. Such ICU telemedicine systems may provide video feeds as well as a transmission of clinical data from instruments in the ICU and may tap the local electronic medical record (EMR) system into which data about the patients may be entered manually. The availability of electronic medical record systems makes it possible to enhance the capability of the remote monitoring physician through the establishment of automated rules at the remote command center which receive clinical data feeds from the EMRs of different ICUs and monitor the clinical data for developing conditions of the ICU patients, for example, by comparing selected data elements against thresholds or monitoring trends in clinical data that may suggest an imminent problem.

The ability to use such telemedicine systems in ICU units is hampered by the need to install compatible software both in the ICU units and the remote command center. Such specialized ICU software can add an unnecessary expense to the local facility and may duplicate functions performed at least in part by the ICU EMR typically shared with a parent hospital and other non-ICU areas of the hospital.

An alternative approach to providing ICU telemedicine, allowing the local EMR system to communicate directly with the remote command center, is hampered by the variety of different types of EMR systems in use in different facilities and the problems attendant to communication with a common remote command center. A variety of EMR systems may present incompatible representations of clinical data encoded into the underlying database of the EMR. A consistent understanding of the data from each ICU is critical for automatic rule systems at the remote command center used to alert an attending physician to patient problems.

Special translation software may be developed to permit the remote command center to properly interpret and display information from each ICU in a consistent manner but developing this necessary translation software for multiple different ICU EMR systems is time-consuming and expensive, and may make the use of a central remote command center impractical for some smaller ICUs which would most benefit from telemedicine. Any translation software will need to be revised periodically as the underlying EMR is upgraded in any way that changes the type or formatting of the contained clinical data, adding to the expense of this approach.

SUMMARY OF THE INVENTION

The present invention provides an ICU telemedicine system that greatly simplifies interfacing with different and often incompatible electronic medical record (EMR) systems. Significantly, the present inventors have recognized that the communication chain of clinical data between the ICU and the remote command center may be divided at a point after at least initial stages in the conversion of the raw data into a decision outcome, and that decision outcome rather than the underlying data may be transmitted to the remote command center. This is possible by downloading or otherwise transferring the analysis rules used by the remote command center to the EMR system of the ICU department. Various aspects of the invention may therefore provide for a significant saving in bandwidth in connecting remote command centers with ICUs, the avoidance of effort in translating data in electronic medical records to a common form for the application of rules, and a simple mechanism to accommodate variations on rules for each facility.

By locating clinical analysis rules at each ICU, the problem of accommodating incompatibilities of varied EMR systems is internalized to the EMR system and thus remains largely invisible to the process of remote command. That is, the ICU EMR effectively performs the work of decoding its own clinical data eliminating the need for multiple customized translation tables for this data at the remote command center. In addition, distributing the clinical analysis rules greatly reduces the amount of data that must be transmitted between the ICU department (and/or their corresponding electronic health record databases) and the remote command center, an important factor when high sampling rates are required for critical patients. Distributing the automatic decision rules allows the monitoring chain to be largely unaffected by internal changes in the ICU EMR system during normal system upgrades and provides freedom for variation of rules among different ICU units as may promote innovation and address different environments or considerations of the ICU departments. Importantly, most electronic medical record systems provide features that permit them to accommodate automatic decision rules as part of their function of allowing automatic report generation and the like.

These particular objects and advantages may apply to only some embodiments falling within the claims and thus do not define the scope of the invention.

DETAILED DESCRIPTION OF THE PREFERRED EMBODIMENT

Figure 1:
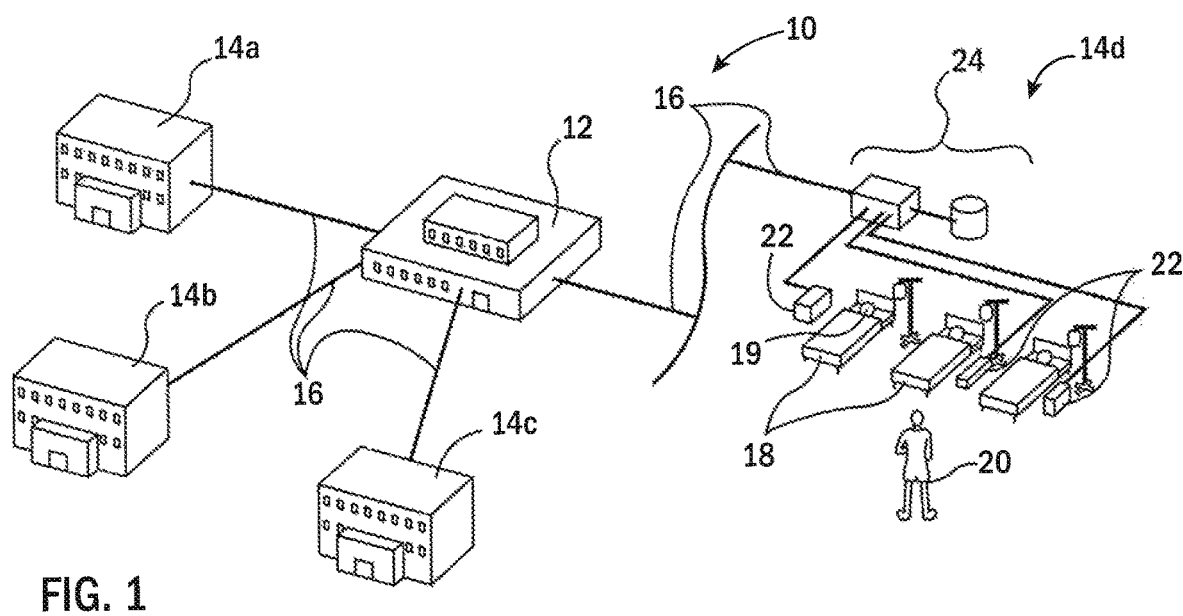
FIG. 1 is a simplified diagram of an ICU telemedicine system providing a remote command center serving multiple ICUs each serving different patients and having a local EMR system.

Referring now to FIG. 1, an ICU telemedicine system 10 may provide for a remote command center 12 typically located in the building separate from multiple local healthcare facilities 14a-14d each holding ICUs and with which the remote command center 12 may communicate over a network 16 (providing for wired or wireless communications). Exemplary local healthcare facilities 14a-14d can include, for example, smaller clinics or hospitals lacking specific expertise necessary for some types of ICU care. The remote command center 12 may be a hospital in a large city or a centrally located facility having a larger diversity of expertise or specialists. Generally the local healthcare facilities 14a-14d will be at a distance from the remote command center 12 that will make difficult physical commuting by healthcare experts from the remote command center 12 to the local healthcare facilities 14a-14d. For example, this separation distance may be more than one half hour and typically many hours or more away by transportation time or more than 10 miles away and typically hundreds of miles away by distance. More fundamentally, the remote command center 12 is separated from the local healthcare facility 14 either by distance or other barriers so as to prevent practical physical access by personnel of the remote command center 12 to the local healthcare facility 14 for the purpose of administering health care. Thus, for example, the remote command center 12 may be only a short distance away but separated in time by the obstacles imposed by separate buildings, elevators, busy streets, etc. Often the remote command center 12 will be separated from the local healthcare facility 14 electrically by the interposition of different networks (for example local area networks) that are incompatible or unconnected except through their connections with a global network such as the Internet. This chain of communication further may include some relatively low bandwidth networks such as radio or satellite links to remote locations.

Each local healthcare facility 14a-14d, for example local healthcare facility 14d, may provide for one or more beds 18 for critical patients 19 and local nursing staff 20 to administer to those patients 19. ICU equipment 22 for monitoring and caring for the patients 19 may be provided including, for example, equipment described above with respect to standard ICU care including: vital signs monitors, patient video monitoring devices, patient pulse monitors, blood sugar monitors, blood pressure monitors, oximeters etc. ICU equipment 22 may further include devices configured to interact with the patient 19, such as a system for administering and/or modifying medication levels, patient notification devices, a patient video conferencing system, etc. Data collected from such ICU equipment 22, for example an intravenous medication administration device such as an infusion pump, may include fluid delivery rate, medication administration rate, administration history, etc.

This ICU equipment 22 may communicate electronically with an electronic medical record (EMR) system 24 serving the local healthcare facility 14d typically not limited to the ICU. Often this ICU equipment 22 connects with the electronic medical record system 24 so that the latter provides essentially the only communication path for obtaining data from the ICU equipment 22. The ICU equipment 22 may provide clinical data such as pulse rate, blood sugar, blood pressure, blood oximetry, and respiration rate. The EMR system 24 may also receive data collected manually by local nursing staff 20, physicians, and other healthcare professionals at the local healthcare facility 14d in addition to the data collected directly from the ICU equipment 22. Examples of data manually entered in the EMR system 24 include assessments by healthcare providers, recordation of a medication administration, a description of the patient's condition, ventilator system settings, conditions met, etc.; some data may be manually or electronically entered including, for example, results of lab tests received electronically from the laboratory (e.g., blood gas testing results, urine testing results, culture results, etc.). In this respect, the EMR system 24 may provide the only comprehensive overview of all data associated with the patient 19.

Generally the EMR system 24 holds clinical medical data, being medical descriptions of the patients 19 as generated as a part of the administration of medical care.

The EMR system 24 may be, for example, of the type manufactured by Epic Systems Corporation of Verona, Wis. under the trade names of EpicCare and Epic, although the present invention anticipates operation with a variety of EMRs 24 that are not necessarily compatible with each other, for example, EMRs 24 from different vendors having data structures or terminology that are not congruent.

Figure 2:
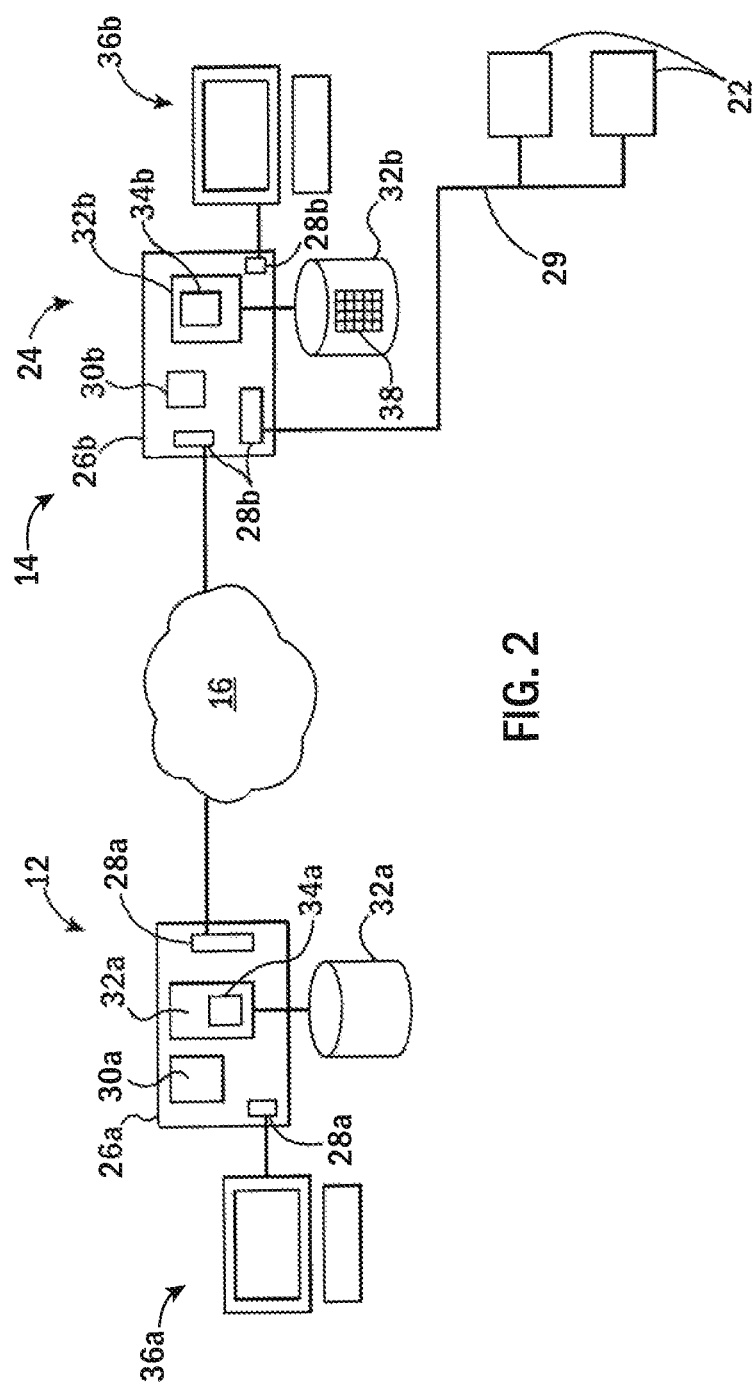
FIG. 2 is a block diagram of the computer systems implementing the ICU telemedicine system of FIG. 1.

Referring now to FIG. 2, generally the remote command center 12 will provide a computer system 26a including a processor 30a and memory system 32a (typically including high-speed random access memory and one or more disk storage units) inter-communicating so as to allow execution of a program 34a in the memory by the processor 30a. The computer system 26a may further include interface circuits 28a communicating with the network 16 and with one or more terminals 36a providing, for example, a graphic display monitor, a keyboard and a mouse and the like, the former for providing information to a healthcare professional in his or her remote command center 12 and the latter receiving commands from that individual in the process of monitoring patients 19 at the local healthcare facilities 14.

In the local healthcare facilities 14, a similar computer system 26b may provide for the functionality of the electronic medical record system 24 and include a processor 30b, memory 32b (holding program 34b), interface circuits 28b, and terminal 36b generally corresponding in function to their similarly numbered counterparts described with respect to the remote command center 12. In this regard, terminal 36b may generally communicate with a keyboard and a cursor control device such as a touchpad or mouse and may include other data entry devices including, for example, a reader such as a barcode reader for scanning medications immediately prior to their administration. The terminal 36 may be a fixed computing device, a portable computing device such as a laptop computer, a tablet computer, a handheld computing device, etc. Patient clinical data for the EMR system 24 may be received from the terminal 36 as manually entered by a healthcare provider or uploaded from a patient medical record representing data obtained about the patient 19 from earlier visits or other healthcare professionals.

One or more of the interface circuits 28b may receive data automatically collected through ICU devices 28 from a local network 29, for example, this data recording the operation of those ICU devices 28 and monitoring critical patient information such as pulse oximetry, pulse rate, respiration rate, blood pressure, temperature and the like. The local network 29 may provide for wireless or wired communication as is well understood in the art. Such automatic data collection may occur on a regular basis at a high update rate commensurate with the dynamic qualities of the data being recorded. For example, pulse rate may be updated every few seconds. This information may be stored in a medical database 38 associated with the EMR system 24 typically in a proprietary format compatible with a database management system implemented by program 34b.

Figure 3:
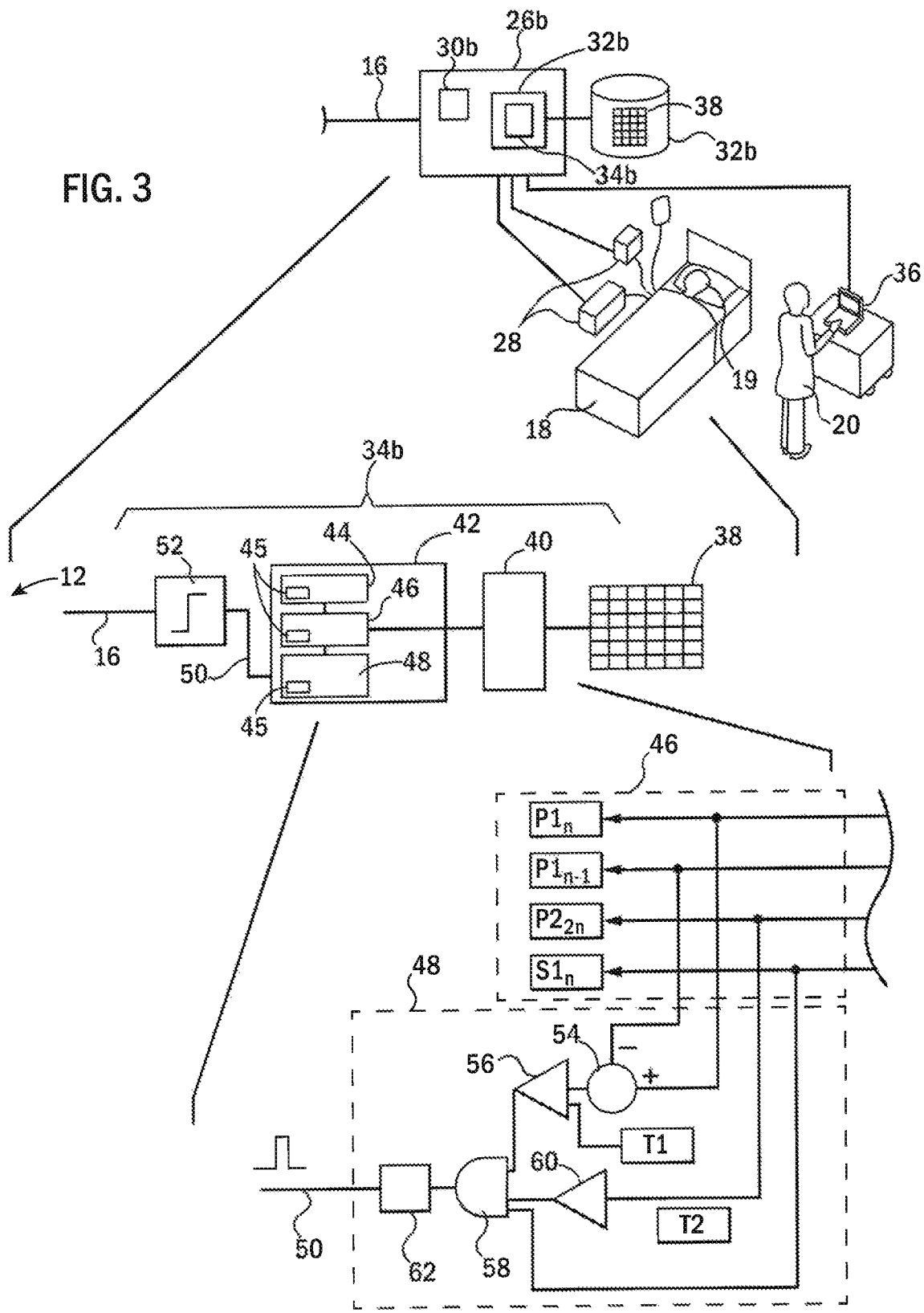
FIG. 3 is an expanded depiction of the ICU computer systems and equipment of FIG. 2 in greater detail, according to an exemplary embodiment.

Referring now to FIG. 3, the EMR system program 34 may generally include a database management system 40 managing the medical database 38 holding the clinical data provided by the staff 20 and collected from the ICU equipment 22. This data supplements the data from the ICU devices 28 and may include, for example, a list of medications being administered to the patient (meds), the results of laboratory tests (labs), or other types of input data available from the EMR such as admit, discharge, transfer (ADT) events, recent emergent surgeries, etc. The database management system 40 generally allows the inputting of data to the medical database 38, together with its proper encoding, indexing and storage, and further allows retrieval of information from the medical database 38 using, for example, queries expressed in a standard query language automatically generated through such queries in one or more predefined reports. The database management system 40 thus operates to allow access to medical records during the normal course of business by the local healthcare facility 14.

The program 34 may further include a rules block 42 that may receive and execute rules to interpret data from the medical database 38. Generally this rules block makes use of pre-existing capabilities of standard EMR systems 24 to run automatic queries for the generation of standard reports, outputs, or the like As implemented in the present invention, the rules block 42 may provide for internal clock 44 for triggering an analysis of the data in the medical database 38 at a regular time, through a query formulator 46 which produces a necessary query that is compatible with the database management system 40 to obtain predefined data required by the desired automatic analysis rules. This data is then provided to a rules engine 48 which will provide a decision outcome 50 based on predetermined rules that may be provided to a network stack 52 for communication over the network 16 with the remote command center 12. It will be appreciated, that this "push" model, with data transfer triggered by the medical database 38, may alternatively be replaced with a "pull" model where the remote command center 12 queries the medical databases 38 on a schedule to obtain data.

Generally, the rules block 42 will receive customized rule information 45 that controls the internal clock 44, the query formulator 46, and the rules engine 48. This customized rule information 45 may include the timing of execution of the rule by the clock 44, formulation of the necessary queries for the query formulator 46 including data needed from the medical database 38 and the proper syntactic structure of the query, and the logic of the rules engine 48, and may be downloaded over the network 16 or may be entered through a local data port or the like manually.

As noted, the rules block 42 may operate in the background as part of program 34 of the EMR system 24 using standard functionality provided by most EMR systems 24 used to generate internal reports, outputs or the like as part of the normal functioning of the local healthcare facility 14. Accordingly the rules block 42 is compatible with most EMR systems without substantial modification of those systems. Compatibility in this sense, means that the rule block allows the implementation of rules having an intended functional goal across many ICU's (e.g. producing a similar output under substantially identical patient conditions), yet in ICU systems employing different EMR technologies and different database structures and/or data terminologies.

Referring still to FIG. 3, the invention contemplates the possibility of a wide variety of different rules being executed by the rules engine 48. An example rule may be formulated generally as a combination of Boolean and arithmetical operations acting on numeric and other data held in the medical database 38. A general rule will make use of both dynamic and static data from the medical database 38, these categories roughly characterizing how fast the data changes. Dynamic data will generally include physiological data such as pulse rate and the like where the data may change on a minute by minute basis (and has clinical significance on this timescale) and typically must be refreshed on the order of 10 minutes or less. Static data may include patient conditions such as diabetes, physical trauma or the like that typically remains the same over a period of hours or days.

In an example rule, the query formulator 46 may be programmed to obtain two data elements: $P1_n$ and $P1_{n-1}$ being physiological data taken at two time samples, for example, current blood pressure and blood pressure five minutes previously. The query formulator 46 may also obtain additional data elements $P2_n$ and $S1_n$ being different physiological dynamic data and static data respectively such as patient pulse rate and general health state (e.g. at risk of circulatory shock) respectively.

The data from the query formulator 46, as received from the database management system 40 after submission of the query, may be passed to the rules engine 48 to be processed to produce a decision outcome 50. In this example, $P1_n$ and $P1_{n-1}$ may be differenced by summing block 54 to determine a trend (e.g. falling blood pressure) and that difference compared by comparator 56 to a predefined threshold (T1) being part of the data 45. The result provides a Boolean output to an AND combiner 58. The value of $P2_n$ may then be compared directly to a second threshold (T2) by comparator 60 to produce a Boolean output to another input of the AND combiner 58. In this example, the third input to the AND combiner 58 may be a state of the patient 19 $S1_n$ in a particular category, for example in this case, as indicating risk of susceptibility to circulatory shock.

The output of the AND combiner 58 may then provide an indication of the coincidence of three necessary conditions for generating an alert, for example, of falling blood pressure, low pulse rate in a patient 19, and susceptibility to circulatory shock. This output may be provided to an edge detector 62 which triggers transmission of the decision outcome 50 to the remote command center 12 alerting a monitoring healthcare professional at the remote command center 12. These particular functional elements will typically be implemented by standard computer instructions.

As noted above, the output of the edge detector may alternatively be stored until a request from the remote command center 12 is received and the output provided only in response to the remote command center instruction if the rule has been satisfied.

This highly simplified rule is intended to show how Boolean and algebraic constructs can be used to construct piles of arbitrary complexity. Comparators 56 and 60 may determine whether an input value is above or below a given threshold and the edge detector 62 may be placed in-line with any parameter or calculation to cause the transmission of a decision outcome 50 only upon change of state if desired. Individual parameters may be subject to both trend analysis and absolute value assessment.

While the above examples describe simple arithmetic and Boolean combinations, it will be appreciated that the rules are not limited to simple mathematical or logical operations on numerical data. For example, the rules may deduce a patient condition, such as "the patient has pneumonia" or "the patient has diabetes". These states may be derived from an analysis of clinical data or from text or data entered by physicians in the EMR, for example, as contained diagnoses found in physician notes or a patient problem list. This analysis may invoke complex processes such as artificial intelligence or other data mining techniques that go beyond simple mathematical or logical statements.

In this respect, the rule may serve to extract general clinical data from the EMR not otherwise characterized. This patient state data, which may have a textural antecedent, may be used alone and reported out as such, or may be used as an input to another rule to be combined with other EMR data according to logical or arithmetic or other rules. In this case, the derived patient state may be used to select among different sub-rules according to the patient diagnosis. For example, reporting thresholds may change according to whether the patient has one or more conditions.

Figure 4:
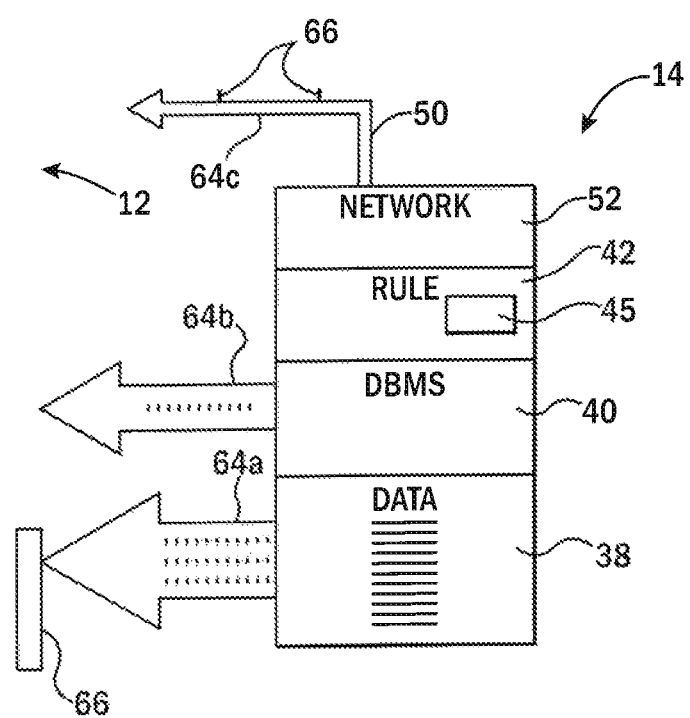
FIG. 4 is a representation of the communication chain between the ICU and the remote command center schematically showing possible data outflows at different links in this chain.

Referring now to FIG. 4, it will be appreciated that the medical database 38, the database management system 40, the rules block 42, and the network circuit 52, present a chain in the transmission of data related to the patients 19 in the local healthcare facilities 14 to the remote command center 12. While data may be transmitted directly from the medical database 38, such data transmissions require a substantial bandwidth 64a and typically a translation of the data into a common form per translation program 66. More generally, data directly from the medical database 38 may adopt any of a variety of different formats for storing data requiring translation or a conversion step practically preventing direct access to access the data at all.

Reduced data transmission can be obtained by communicating with the medical database 38 through the database management system 40 to provide for selective data properly interpreted by the database management system 40 decreasing bandwidth 64b in response to the need for transmission of a specialized query from the remote command center 12.

In contrast, the present invention's transmission of a decision outcome 50 provides a much reduced bandwidth 64c and eliminates the necessity of a translation program 66 at the remote command center 12.

By transmitting only upon changes in decision outcome 50, a further bandwidth reduction may be achieved. The term "bandwidth" as used herein comports with the generally understood concept combining an amount of data transmitted and the speed of data transmission.

Figure 5:
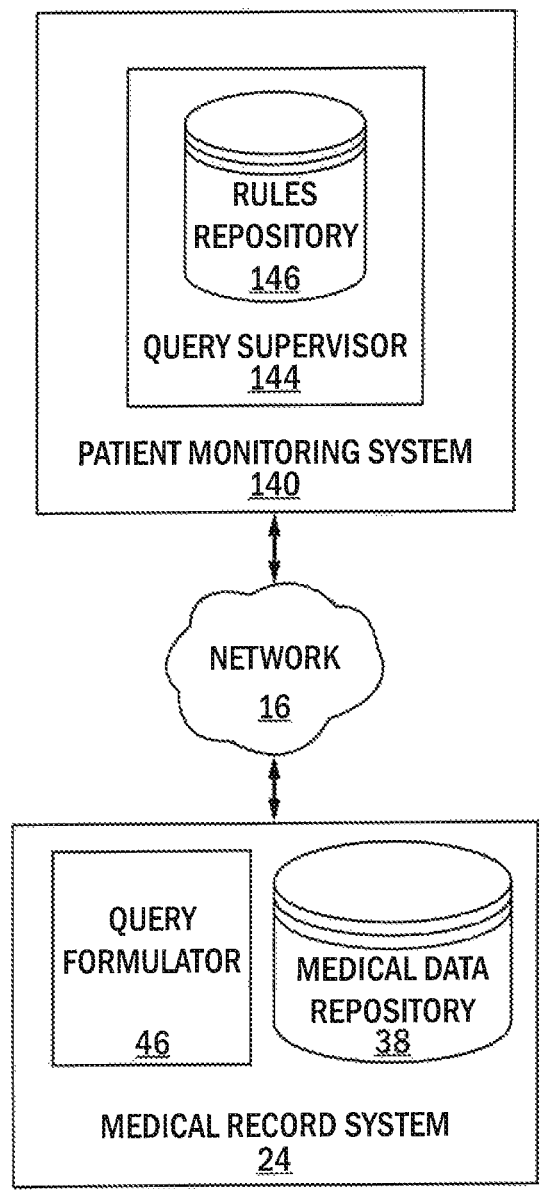
FIG. 5 is a block diagram of one embodiment of the ICU telemedicine system of FIG. 1 providing a downloading of rules from the remote command center.

Referring now to FIG. 5, a simplified representation of the EMR system 24, including a medical data repository in the form of medical database 38, in communication with a patient data monitoring system 140 over network 16, is shown, according to an exemplary embodiment. Network 16, as noted above, may be any type of communication network, such as the Internet, allowing medical record system 24 to communicate with monitoring system 140. Although only a single medical record system 24 is shown, it should be understood that patient monitoring system 140 may be configured to communicate with a large number of systems 24 to provide remote patient monitoring services from a central location to multiple remote locations. Further, although shown and described as being implemented by system 24, the present system and method may be implemented by an ancillary computing device communicating with the system 24.

In order to provide patient clinical data to monitoring system 140, medical record system 24 may be configured to implement a query response engine in the form of the query formulator 46 configured to interact with monitoring system 140. Query formulator 46 may be software configured to implement rules on the local system to efficiently provide patient clinical data to monitoring system 140 in response to one or more queries sent by query supervisor 144 having a rules repository 146, as described below in further detail with reference to FIGS. 6-7.

Arden syntax is one possible grammar for representing and processing medical conditions and recommendations embodied in medical algorithms. A patient monitoring rule may be a medical logic module written in Arden syntax that is called by the query formulator 46 when manually triggered or when the condition it is written to detect occurs. Detecting a condition may be triggered based on data stored in medical database 38, data being received from a monitoring device or manually entered by a healthcare provider, etc. as described above Implementing rules on EMR system 24 may include retrieving and transmitting a subset of stored clinical data for a patient 19 from medical database 38. Implementing rules on system 24 may further include generating new clinical data based on the stored clinical data for a patient 19. One example of generating new clinical data may include, for example, generating a priority code indicating the likelihood that the patient 19 will need attention from a healthcare provider based on patient clinical data. Another example may include generating an advisory where the patient clinical data indicates that the patient 19 may have a specific medical condition. An advisory may be presented as a risk score, a priority ranking, etc. to present information indicative of the level of a patient's risk of deterioration, the urgency of actions that are recommended for the patient 19, etc. Another example may include generating one or more potential diagnoses based on the patient clinical data.

Query formulator 46 may be a software application implemented by medical record system 24. The rules used by the query formulator 46 may be an installed component of system 24, may be received from monitoring system 140 during an initial communication protocol, may be received as a component of a request for specific information from monitoring system 140, etc., as is also described in further detail below.

Query formulator 46 may be configured to receive a request for patient status information from the monitoring system 140. According to one embodiment, the request is for data that is less than the complete data set for the patient 19 being monitored. Accordingly, rather than duplicating copious clinical data for transmittal and storage on monitoring system 140, query formulator 46 is configured to locally run one or more patient monitoring rules on system 24 and generate a rule response that includes patient data that is less than the complete set of patient clinical data stored in medical database 38.

Figure 6:
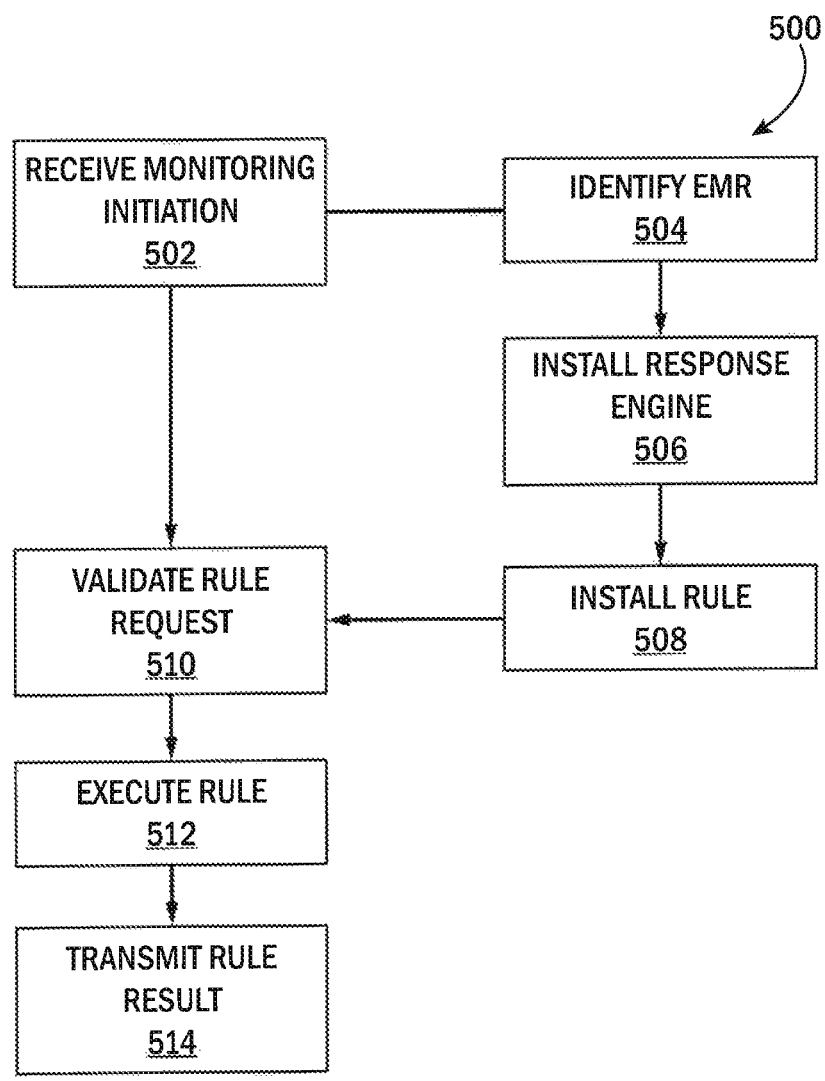
FIG. 6 is a flowchart illustrating a series of steps of programs executed by the computers of FIG. 2 for configuring the ICU telemedicine system according to this embodiment.

Referring now to FIGS. 5 and 6, a flowchart 500 illustrating a series of steps to be performed in a method for initiating a remote monitoring process is shown, according to an exemplary embodiment. In implementing the steps illustrated in flowchart 500, a query formulator 46 operating on the medical record system 24 and in communication with the monitoring system 140, establishes a set of data linkages between these components permitting the monitoring system 140 to receive information from system 24 during a remote monitoring period for a patient 19. Although specific steps are shown in flowchart 500 as being performed in a specific order, it should be understood that the method may be performed using more, fewer, and/or a different ordering of steps to implement the systems and methods described herein.

In a step 502, remote patient monitoring is initiated. Initiation of remote patient monitoring may be performed by, for example, executing a program using medical record system 24 and/or patient monitoring system 140. For example, according to an exemplary embodiment, a healthcare provider at a remote command center 12 may initiate remote patient monitoring to be performed by the local healthcare facility 14. In response, system 24 may be configured to transmit an initiation request to monitoring system 140. The initiation request may be configured to include the information required to initiate patient monitoring including, for example, a patient identifier, a medical record system 24 identifier, security information, a healthcare provider identifier, etc.

Following initiation, data communication between systems 24 and 140 may be implemented using a secure data synchronization protocol. Examples of systems for implementing secure data synchronization are described in U.S. patent application Ser. No. 10/794,933, filed Mar. 5, 2004 and U.S. patent application Ser. No. 12/412,535, filed Mar. 27, 2009, both of which are hereby incorporated by reference in their entirety.

Generally, system 140 transmits the security information to the medical record system 24 providing the authority for system 140 to access the records of the medical database 38 of the medical record system 24. Such security information may include identification and password information, for example, manually entered through the keyboard of the patient care computing terminal 36a. Alternatively, this security information may be provided using more advanced authentication techniques such as establishing a secure communication channel. The security information may be later received by an authentication module, typically implemented in software in the medical record system 24, blocking access to the medical record system 24 where unauthorized.

During initiation of the patient monitoring communication channel, system 140 may be configured to determine whether medical record system 24 is configured for remote patient monitoring. Wherein medical record system 24 is configured for remote patient monitoring, system 140 may proceed to patient monitoring step 502.

Where medical record system 24 is not already configured for remote patient monitoring, in a step 504, monitoring system 140 may be configured to identify the particular medical record system being implemented by the remote location. Monitoring system 140 is configured to identify the medical record system to determine whether the local healthcare facility 14 is implementing a compatible medical record system 24 or incompatible medical record system 24.

Monitoring system 140 may be further configured to determine whether the remote location medical record system has installed a query formulator 46. If not, and based on the identification of the medical record system in step 504, monitoring system 140 may be configured to transmit for installation, a system specific query formulator 46 in a step 506.

Monitoring system 140 and/or query formulator 46 may further be configured to include one or more rules for instantiation and implementation within query formulator 46 in a step 508. According to an exemplary embodiment, the specific rules may be dependent on the type of patient monitoring to be performed as indicated during monitoring initiation step 502. Further, the specific rules may be dependent on the type of medical record system implemented by medical record system 24.

Rules repository 146 may be configured to include multiple instantiations of each type of rule depending on the type of electronic medical record system to be monitored. For example, a rules repository may include multiple rules for various known Arden-compliant decision support applications. Typically, rules may be associated with specific medical logic modules that are customized for specific use in a proprietary environment. The rules repository 146 may provide for different rules for different local healthcare facilities 14 allowing variation and experimentation among different healthcare settings.

Rules repository 146 may further include sets of rules organized in tiers of priority. For example, a first tier may include rules requiring an immediate interruption, such as when a patient 19 had been administered an antibiotic that is known to be ineffective for a diagnosed infection noted in medical database 38. A second tier may include rules requiring checking based on a time period, such as every four hours, to monitor a patient's condition using known best practices. A third tier may include rules that are not associated with specific timing, but are known to be good practices, such as determining whether received data from monitoring ICU equipment 22 correlates with information stored in medical database 38, indicating good documentation practices, whether a patient 19 with the flu has been properly elevated, etc. A fourth tier may include rules associated with known risk conditions, such as removal of a patient 19 from a ventilator, etc.

In performing remote patient monitoring, patient monitoring system 140 may periodically transmit a rule execution request to request patient clinical data contained within records of the medical database 38 stored in the memory 32 of the medical record system 24 that the healthcare provider wishes to access, as indicated by process block 510. Patient information may also be transmitted based on detected changes in the condition of patient 19, based on specific requests, based on one or more advisory conditions, based on periodic monitoring, etc. Information requests may be implemented by system 140 by transmitting a rule execution request to the query formulator 46. Each rule execution request may be configured to include patient identification information. Query formulator 46 is configured to receive and execute a rule based upon the contents of the rule execution request in a step 512, as described in further detail below with reference to FIG. 7.

According to an exemplary embodiment, a rule execution request may be configured to request information related to one or more patients 19. For example, a rule execution request may be configured to request specific information for a single patient 19 based on a diagnosis associated with that patient 19. Alternatively, a rule execution request transmitted hourly may be configured to request updated vital sign data for all patients 19 being monitored at the remote healthcare facility.

Figure 7:
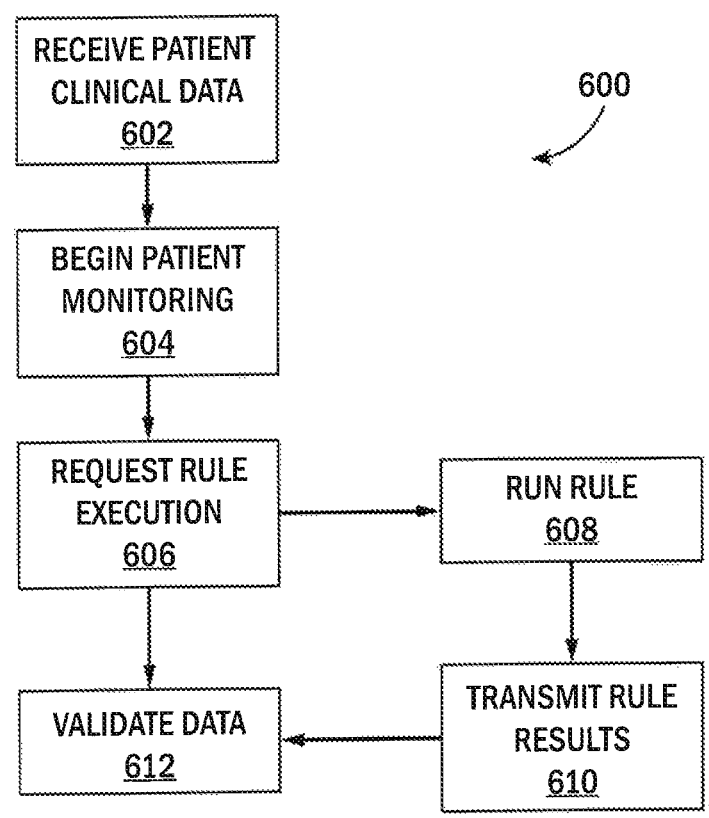
FIG. 7 is a flowchart illustrating the steps of programs executed by the computers of FIG. 2 in providing patient monitoring data in response to a rule execution request, according to an exemplary embodiment.

Referring now to FIG. 7, a flowchart 600 illustrating a method for providing patient monitoring data in response to a rule execution request to be implemented by query formulator 46 is described in further detail, according to an exemplary embodiment. A rule execution request may include a variety of types of information, including, but not limited to, a list of patients 19 for whom rules are to be executed, a listing of rules to be executed, a ranking of rule execution priority, a listing of rule execution timing, etc.

In a step 602, medical record system 24 is configured to continuously receive updated information for one or more patients 19 being cared for by a healthcare provider, such as remote command center 12 or local healthcare facility 14. Exemplary information can include output from any patient monitoring device 22 information provided by one or more healthcare providers such as observation data, test results, transcription of patient information received orally from the patient 19, etc.

In a step 604, query formulator 46 may be configured to receive a request to begin remote patient monitoring. Remote patient monitoring may be initiated using a variety of methods, including, for example, transmitting a request from query formulator 46 to patient monitoring systems 140, receiving one or more rule execution requests at query formulator 46 from patient monitoring system 140, manual initiation by a healthcare provider using a medical record system 24, etc.

In a step 606, a query formulator 46 may be configured to receive a rule execution request. The rule execution request may be transmitted from patient monitoring system 140 and/or may be initiated locally. The execution request may be initiated locally based on a detected change in the condition of the patient 19, based on elapsed time, based on a manual request by a healthcare provider, etc.

In a step 608, query formulator 46 is configured to execute one or more rules in response to the received rule execution request. Executing a rule may include receiving data from medical database 38, generating data based on a plurality of inputs, requesting data from a healthcare provider, etc.

In a step 610, query formulator 46 is configured to generate and transmit rule execution results. The rule execution results may include data copied directly from an electronic medical record of the patient 19 stored within medical database 38, where the data is less than all of the available data for patient 19. The rule execution results may further be configured to include calculated information generated based on the data stored within medical database 38.

In a step 612, the patient monitoring system 140 is configured to receive the transmitted rule execution results. Transmitted rule execution results may be analyzed by system 140 to generate a monitoring priority ranking. The priority ranking may be generated based on the received data and known best practices. One such example may include recognition that the received results indicate one or more patient conditions that require intervention by a healthcare provider.

Referring again to FIG. 6, after rule execution, clinical medical data may be exchanged between the EMR system 24 and the remote command center 12 in a step 514, with data input at the patient care terminal 36b passing to the medical database management system 40 to be entered into the records of the medical database 38 within the memory 32, and data from the memory 32, as processed by the query formulator 46, being transmitted to the remote command center 12.

The present invention has been described in terms of the preferred embodiment, and it is recognized that equivalents, alternatives, and modifications, aside from those expressly stated, are possible and within the scope of the appended claims.

We claim:
1. A telemedicine system including a remote site and a plurality of patient monitoring facilities, comprising:
a patient monitoring telemedicine system at each of the plurality of patient monitoring facilities, each patient monitoring telemedicine system including
a patient monitoring database system for receiving and storing clinical data related to at least one patient in accordance with a database type that defines data structures or terminology used by the database system;
a patient monitoring computer system in communication with the patient monitoring database system and with the remote site, the patient monitoring computer system programmed to execute a stored program held in non-transient media to:
(a) receive a query formulator inquiry from the remote site;
(b) transmit a query formulator response to the remote site indicating whether the patient monitoring computer system includes a query, formulator;
(c) receive and instantiate a query formulator from the remote site based on the negative query formulator response, wherein the query formulator is system specific to the database type of the patient monitoring telemedicine system;
(d) receive at least one rule from the remote site, the rule defining one or more decision outcomes to be generated when clinical data satisfies one or more clinical parameters for the decision outcome;
(e) generate a plurality of data requests for each received rule, each data request
1) using data protocols using the data structures or terminology compatible with the database type of the patient monitoring telemedicine system, and
2) correlated to a single clinical data entry from at least one of the patient monitoring database system related to the at least one patient in the patient monitoring facility;
(f) executing the received rule including execution of the plurality of data requests and application of the rule to data entries provided based on the execution of the data requests to generate a decision outcome; and
(g) transmitting the generated decision outcome to the remote site, wherein the patient monitoring database system of at least one of the plurality of patient monitoring facilities has a database type that is a different database type from at least one of the remaining patient monitoring facilities.

2. The telemedicine system of claim 1, wherein the patient monitoring facilities and the remote site are separated so as to prevent direct physical administration of care to the one patient by an individual at the remote site.

3. The telemedicine system of claim 2, wherein the patient monitoring database includes clinical data generated by at least one patient device selected from the group consisting of a vital sign monitor, a patient pulse monitor, blood sugar monitor, ventilator, dialysis equipment, defibrillator, respirator, and fetal monitor.

4. The telemedicine system of claim 3, wherein the clinical data further includes a medical description of a patient generated as part of an administration of medical care to the patient.

5. The telemedicine system of claim 4, wherein the rule combines numeric representations of the clinical data according to logical and arithmetic operations to produce a Boolean value or a numeric value or range.

6. The telemedicine system of claim 5, wherein the rule is formulated from at least one of an arithmetic and Boolean operation.

7. The telemedicine system of claim 5, wherein the rule extracts a patient condition from the clinical data.

8. The telemedicine system of claim 6, wherein the clinical data is selected from the group consisting of pulse rate, blood pressure, blood oximetry, and respiration rate.

9. The telemedicine system of claim 1, wherein the decision outcome is transmitted only on changes in the decision outcome.

10. The telemedicine system of claim 2, wherein the stored program further comprises instructions to receive a rule definition for a new rule, the rule definition including instructions to the patient monitoring computer system for performing a new data request by identifying the patient device and defining parameters for the patient monitoring computer system to obtain the clinical data.

11. A telemedicine system including a remote site and a plurality of patient monitoring facilities, each having a patient, monitoring telemedicine system, comprising:
  a remote site monitoring computer system, including a patient medical data query engine configured to generate one or more rule execution requests;
  a query formulator configuration system programmed to execute a query formulator configuration program held in non-transient media to:
  receive a remote medical monitoring inquiry from a patient monitoring telemedicine system,
  transmit a query formulator inquiry to the patient monitoring telemedicine system,
  (c) receive a query formulator response from the patient monitoring telemedicine system indicating the patient monitoring telemedicine system lacks a query formulator, and
  (d) transmit a query formulator to the patient monitoring telemedicine system based on the negative query formulator response, wherein the query formulator is system specific to a database type of the patient monitoring telemedicine system,
  wherein the remote site monitoring system transmits at least one rule execution request to the patient monitoring telemedicine system including at least one rule defining one or more decision outcomes to be generated when clinical data satisfies one or more clinical parameters for the decision outcome, and
  wherein the transmitted query formulator is programmed to execute a query formulator stored program held in non-transient media to generate a plurality of data requests for received rule execution requests, each data request using data protocols using the data structures or terminology compatible with the database type of the patient monitoring telemedicine system and correlated to a single clinical data entry related to at least one patient at the patient monitoring facility.

12. The system of claim 11, wherein the rule execution, requests include a request for periodic rule execution.

13. The system of claim 11, wherein the remote site monitoring system is configured to monitor the clinical data and transmit an additional rule request based on a detected change in the monitored clinical data.

14. The system of claim 11, wherein the clinical data includes data from a patient monitoring device.

15. The system of claim 14, wherein the patient monitoring device is selected from the group consisting of a vital sign monitor, a patient pulse monitor, blood sugar monitor, ventilator, dialysis equipment, defibrillator, respirator, and fetal monitor.

16. The system of claim 11, wherein the patient monitoring telemedicine system is further configured to translate the patient clinical data from a first format to a second format based on the rule execution request.

17. The system of claim 11, wherein the decision outcome is one of a diagnosis and a patient priority ranking.

18. The system of claim 17, wherein the decision outcome is received based on detected changes in the decision outcome.

* * * * *